United States Patent [19]
Dust et al.

[11] Patent Number: 5,386,042
[45] Date of Patent: Jan. 31, 1995

[54] PREPARATION OF 1,4-DIAMINOANTHRAQUINONE-2,3-DISULFONIC ACID AND 1,4-DIAMINOANTHRAQUINONE-2,3-DINITRILE

[75] Inventors: Matthias Dust, Ludwigshafen; Udo Bergmann, Bensheim; Gerd Schwantje, Wachenheim, all of Germany

[73] Assignee: BASF Aktiengesellschaft, Ludwigshafen, Germany

[21] Appl. No.: 88,740

[22] Filed: Jul. 8, 1993

[30] Foreign Application Priority Data

Jul. 8, 1992 [DE] Germany ............... 4222302

[51] Int. Cl.⁶ ............................................. C07C 303/00
[52] U.S. Cl. ..................................... 552/239; 552/225
[58] Field of Search ............................... 552/225, 239

[56] References Cited

U.S. PATENT DOCUMENTS

| | | | |
|---|---|---|---|
| 4,042,605 | 8/1977 | Hartwig | 552/249 |
| 4,279,825 | 7/1981 | Schmitz . | |
| 4,749,521 | 6/1988 | Hattori et al. | 552/225 |

FOREIGN PATENT DOCUMENTS

| | | | |
|---|---|---|---|
| 416940 | 9/1934 | United Kingdom | 552/225 |
| 2034737 | 6/1980 | United Kingdom . | |

OTHER PUBLICATIONS

Patent Abstracts of Japan, vol. 6, No. 266 (C-142) (1144), Dec. 25, 1982, JP-A-57 158 261, Sep. 30, 1982.
Chemical Abstracts, vol. 100, No. 16, Apr. 1984, An 122764f, "1,4-Diaminoanthraquinone-2,3-Disulfonic Acid".

*Primary Examiner*—Johann Richter
*Assistant Examiner*—Rebecca Cook
*Attorney, Agent, or Firm*—Oblon, Spivak, McClelland, Maier, & Neustadt

[57] ABSTRACT

1,4-Diaminoanthraquinone-2,3-disulfonic acid (I) is prepared by reacting 1,4-diamino-2,3-dihaloanthraquinone (II) with boric acid in an inert organic solvent and further reacting the resulting reaction product (IIa) with an aqueous sulfite solution, by a method in which the inert organic solvent used is a nonpolar solvent having a boiling point of $\geq 130°$ C. and a density of $\leq 0.95$ g/cm$^3$, and 1,4-diaminoanthraquinone-2,3-dinitrile (III) is prepared by reacting the 1,4-diaminoanthraquinone-2,3-disulfonic (I) with a cyanide.

6 Claims, No Drawings

PREPARATION OF 1,4-DIAMINOANTHRAQUINONE-2,3-DISULFONIC ACID AND 1,4-DIAMINOANTHRAQUINONE-2,3-DINITRILE

The present invention relates to an improved process for the preparation of 1,4-diaminoanthraquinone-2,3-disulfonic acid (I) by reacting a 1,4-diamino-2,3-dihaloanthraquinone (II) with boric acid in an inert organic solvent and further reacting the resulting reaction product with an aqueous sulfite solution.

The present invention furthermore relates to the preparation of 1,4-diaminoanthraquinone-2,3-dinitrile (III) by reacting the 1,4-diaminoanthraquinone-2,3-disulfonic acid (I) obtained according to the invention with cyanide.

1,4-Diaminoanthraquinone-2,3-disulfonic acid (I) and 1,4-diaminoanthraquinone-2,3-dinitrile (III)

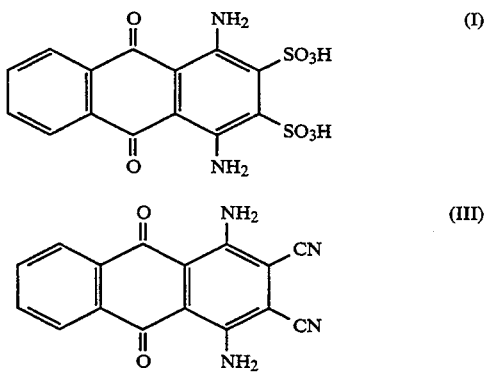

are useful intermediates for the preparation of blue disperse dyes, such as C.I. Disperse Blue 60.

U.S. Pat. No. 4 279 825 discloses the preparation of 1,4-diaminoanthraquinone-2,3-disulfonic acid starting from 1,4-diamino-2,3-dichloroanthraquinone. There, the dichloroanthraquinone is first reacted with boric acid in the presence of nitrobenzene, the water formed in the reaction being distilled off completely as a mixture with the nitrobenzene. The reaction product (IIa) of anthraquinone and boric acid occurs as an intermediate and is isolated and then reacted with aqueous sulfite to give the disulfonic acid.

The disadvantage of this process is that the steam-volatile boric acid which is used in excess is also expelled at the same time when nitrobenzene and water are distilled off and may lead to blockage of the particular apparatus. When the paddle drier recommended in U.S. Pat. No. 4 279 825 is used for drying the intermediate (IIa), further problems occur owing to the highly corrosive action of the reaction mixture.

The disulfonic acid (II) can then be converted into the dinitrile (III) by reaction with cyanide, as described in, for example, U.S. Pat. No. 4 279 825.

It is an object of the present invention to prepare 1,4-diaminoanthraquinone-2,3-disulfonic acid (I) without the stated disadvantages in good yield and purity by a method which is economical and simple in terms of process engineering and hence also to permit advantageous preparation of 1,4-diaminoanthraquinone-2,3-dinitrile (III).

We have found that this object is achieved by a process for the preparation of 1,4-diaminoanthraquinone-2,3-disulfonic acid (I) by reacting a 1,4-diamino-2,3-dihaloanthraquinone (II) with boric acid in an inert organic solvent and further reacting the resulting reaction product (IIa) with an aqueous sulfite solution, wherein the inert organic solvent used is a nonpolar solvent having a boiling point of $\geq 30°$ C. and a density of $\leq 0.95$ g/cm$^3$.

The 1,4-diaminoanthraquinone-2,3-disulfonic acid (I) prepared according to the invention can then be converted into 1,4-diaminoanthraquinone-2,3-dinitrile (III) by reaction with a cyanide.

Nonpolar organic solvents which are suitable for the reaction of the 1,4-diamino-2,3-dihaloanthraquinone (II) with boric acid generally have a boiling point of $\geq 130°$ C.

In addition to aliphatic hydrocarbons or mixtures thereof, as are commercially available, for example, under the name Exsol ® (Esso Chemie), aromatic hydrocarbons, in particular alkylbenzenes, which boil above 130° C., are particularly preferred. Examples of particularly preferred alkylbenzenes are m-, p- and o-xylene and mixtures thereof, ethylbenzene and isopropylbenzene. The use of suitable mixtures of alkylbenzenes, which are available, for example, under the name Solvesso ® (Esso Chemie), is particularly advantageous. Mixtures having a boiling range from about 180° to 200° C. and a density of about 0.90 g/cm$^3$ (Solvesso 150) are very particularly preferred.

There is in principle no upper limit for the boiling point of the solvent, but, for practical reasons, the hydrocarbons boiling at above 250° C. are not used as a reaction medium owing to their high viscosity. In order to achieve an economical reaction rate, the boiling point of the solvent should be $\geq 130°$ C., preferably $\geq 140°$ C.; the temperature range especially preferred is from about 160° to 220° C.

It would also be possible to use alkylbenzenes boiling below 130° C. The reaction would take place, but with an uneconomically low reaction rate.

Furthermore, the density of the solvent should be lower than that of an aqueous phase, in particular, that in the sulfonation reaction, i.e. the density should be in general $\leq 0.95$ g/cm$^3$.

The particular advantage of using the solvents according to the invention is that they need not be separated off before the sulfonation reaction but the intermediate (IIa) obtained from the anthraquinone (II) and boric acid can be reacted without intermediate isolation, directly in the form of the resulting reaction mixture, with sulfite to give the disulfonic acid (III). The solvent can then be separated off in a simple manner as the light phase and can be reused as solvent. The problems described for the process of U.S. Pat. No. 4,279,825 do not arise at all in the novel process since it is possible to dispense with the isolation of the intermediate (IIa).

The amount of solvent according to the invention, in particular alkylbenzene, is not critical per se; as a rule, from 3 to 5 kg are used per kg of (II).

The process conditions usually used for this reaction may be chosen for the further process conditions.

Preferred starting compounds (II) are both 1,4-diamino-2,3-dichloroanthraquinone and 1,4-diamino-2,3-dibromoanthraquinone.

The boric acid can be used in the form of meta-boric acid (HBO$_2$) or in the form of the preferred ortho-boric acid (H$_3$BO$_3$).

In general, the amount of boric acid is from 2 to 10, preferably from 6 to 8, mot per mol of II.

In an advantageous process, the mixture of 1,4-diamino-2,3-dihaloanthraquinone (II), boric acid and solvent according to the invention is heated in the course of from about 1 to 3 hours to 120°–180° C., preferably 150°–165° C., if desired under an inert gas, for example while passing a stream of nitrogen through. Some of the water of reaction and some of the solvent distills off as an azeotropic mixture during this procedure. After a reaction time of from about 2 to 3 hours, during which the reaction product (IIa) of haloanthraquinone (II) and boric acid has formed, the reaction mixture is cooled to, as a rule, 90° to 95° C. and is used without further treatment for the formation of the disulfonic acid (I).

The sulfonation reaction itself can likewise be carried out under the conventional conditions.

Especially suitable aqueous sulfites are solutions of alkali metal sulfites, such as potassium sulfite and in particular sodium sulfite, as well as ammonium sulfite.

In general, the sulfite is used in an amount of from about 2.2 to 2.6 mol per mol of (II), as an aqueous solution of from about 8 to 10% strength by weight.

During the addition of the resulting reaction mixture to the sulfite solution heated to 90° to 95 ° C., the pH of the mixture is advantageously kept at from 7.5 to 8.5 by simultaneously metering in a base, such as sodium hydroxide solution or potassium hydroxide solution.

This reaction generally takes from-about 30 to 60 minutes.

In the novel process, the nonpolar solvent still present is subsequently separated off as the light phase from the lower aqueous phase containing the disulfonic acid (I) as a dissolved salt, this step preferably being effected after clarifying filtration of the total batch.

Isolation of the 1,4-diaminoanthraquinone-2,3-disulfonic acid (I) by precipitation with an acid, filtration, washing and drying can be dispensed with; instead, the isolated, aqueous phase can advantageously be used directly for subsequent reactions in aqueous medium, such as the preparation of 1,4-diaminoanthraquinone-2,3-dinitrile (III).

The novel process for the preparation of 1,4-diaminoanthraquinone-2,3-disulfonic acid (I) can be carried out either continuously or batchwise.

With the aid of said process, the 1,4-diaminoanthraquinone-2,3-disulfonic acid is obtained in a simple, economical manner in good yield and high purity, which is also reflected in the quality and yield of the secondary products.

For the further reaction to give 1,4-diaminoanthraquinone-2,3-dinitrile (III), it is possible to proceed in the conventional manner described in U.S. Pat. No. 4 279 825, by adding an alkali metal cyanide such as potassium cyanide or in particular sodium cyanide, in an amount of, as a rule, from 2.2 to 4 mol per mol of (I), heating the resulting mixture at from 90° to 95° C. for from about 3 to 5 hours and destroying excess cyanide with the aid of hydrogen peroxide.

1,4-Diaminoanthraquinone-2,3-dinitrile (III), too, is obtained in such high purity that it can be used directly for further purposes, such as pigment preparation.

The preparation of 1,4-diaminoanthraquinone-2,3-dinitrile (III) via the novel sulfonation of a 1,4-diamino-2,3-dihaloanthraquinone (II) and subsequent reaction of the resulting 1,4-diaminoanthraquinone-2,3-disulfonic acid (I) with cyanide is an advantageous synthesis route.

EXAMPLE 1 a) Preparation of 1,4-diaminoanthraquinone-2,3-disulfonic acid (I)

A mixture of 400 g of Solvesso 150, 103 g (0.26 mol) of 1,4-diamino-2,3-dibromoanthraquinone (calculated as 100%) and 139 g (2.24 mol) of ortho-boric acid was heated to 160°–165° C. in the course of 3 hours under a gentle stream of nitrogen. A water/Solvesso 150 mixture distilled off slowly.

After 2 hours, the suspension was cooled to 90° C. and was added dropwise to a solution of 80 g of sodium sulfite in 1200 ml of water, said solution being at 90° C. The pH of the solution was kept at from 8 to 8.5 during the entire time of introduction by the simultaneous dropwise addition of 50% strength by weight sodium hydroxide solution.

After being stirred for 30 minutes at 90° C., the total reaction batch was subjected to clarifying filtration, and the solvent was separated off by phase separation. The remaining aqueous solution contained the 1,4-diaminoanthraquinone-2,3-disulfonic acid.

b) Further reaction to give 1,4-diaminoanthraquinone-2,3-dinitrile (III)

After the addition of 36 g (0.73 mol) of sodium cyanide, the aqueous phase was heated at from 90° to 95° C. for 3 hours. It was cooled to 80° C., after which 120 ml of 30% strength by weight hydrogen peroxide were added dropwise to destroy excess cyanide.

The resulting precipitate was filtered off while hot, washed with hot water and dried.

65.3 g of 1,4-diaminoanthraquinone-2,3-dinitrile having a purity of 91.4% were obtained, which corresponds to a yield of 79.5%.

Example 2

80.0 g (0.26 mol) of 1,4-diamino-2,3-dichloroanthraquinone (calculated as 100%) in 480 g of Solvesso 150 were reacted similarly to Example 1.

In the further reaction of the resulting 1,4-diaminoanthraquinone-2,3-disulfonic acid, 64 g of 1,4-diaminoanthraquinone-2,3-dinitrile having a purity of 90% were obtained, which corresponds to a yield of 77%.

We claim:

1. A process for the preparation of 1,4-diaminoanthraquinone-2,3-disulfonic acid (I) by reacting a 1,4-diamino-2,3-dihaloanthraquinone (II) with boric acid in an inert organic solvent and further reacting the resulting reaction product (IIa) with an aqueous sulfite solution, wherein the inert organic solvent used is a nonpolar solvent having a boiling point of $\geq 130°$ C. and a density of $\leq 0.95$ g/cm$^3$.

2. A process as claimed in claim 1, wherein the solvent used is an alkylbenzene or alkylbenzene mixture.

3. A process as claimed in claim 1, wherein the reaction product (IIa) is reacted without intermediate isolation, in the form of the resulting reaction mixture, with the sulfite, and the organic solvent is then removed by phase separation.

4. A process as claimed in claim 1, wherein the 1,4-diamino-2,3-dihaloanthraquinone (II) used is 1,4-diamino-2,3-dichloroanthraquinone or 1,4-diamino-2,3-dibromoanthraquinone.

5. A process for the preparation of 1,4-diaminoanthraquinone-2,3-dinitrile (III) by a) reacting a 1,4-diamino-2,3-dihaloanthraquinone (If) with boric acid in an inert organic solvent and further reacting the resulting reaction product (IIa) with an aqueous sulfite solution and b) subsequently reacting the resulting 1,4-diaminoanthraquinone-2,3-disulfonic acid (I) with cyanide, wherein the inert organic solvent used in step a) is a nonpolar solvent having a boiling point of $\geq 130°$ C. and a density of $\geq 0.95$ g/cm$^3$.

6. A process as claimed in claim 5, wherein the solvent used is an alkylbenzene or alkylbenzene mixture.

* * * * *